(12) United States Patent
Stoertz et al.

(10) Patent No.: US 11,610,675 B1
(45) Date of Patent: Mar. 21, 2023

(54) DYNAMIC AND TARGETED ALLOCATION OF RESOURCES FOR COACHING SERVICE

(71) Applicant: Verily Life Sciences LLC, Mountain View, CA (US)

(72) Inventors: Aaron Haywood Stoertz, Redwood City, CA (US); Nikhil Roy, Sunnyvale, CA (US); David Wright, Burlingame, CA (US); Peilun Shan, San Francisco, CA (US); Katherine Nadell, San Jose, CA (US); Sarah Abramson, Mountain View, CA (US); Jesse Elds, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 124 days.

(21) Appl. No.: 16/989,122

(22) Filed: Aug. 10, 2020

Related U.S. Application Data

(60) Provisional application No. 62/884,981, filed on Aug. 9, 2019.

(51) Int. Cl.
*G16H 40/67* (2018.01)
*G16H 20/60* (2018.01)
(Continued)

(52) U.S. Cl.
CPC ............ *G16H 40/67* (2018.01); *G09B 5/125* (2013.01); *G09B 5/14* (2013.01); *G16H 20/30* (2018.01); *G16H 20/60* (2018.01); *G16H 50/30* (2018.01)

(58) Field of Classification Search
CPC ........ G16H 20/30; G16H 50/30; G16H 20/60; G16H 40/67; G09B 5/125; G09B 5/14; G06Q 50/20–26
See application file for complete search history.

(56) References Cited

U.S. PATENT DOCUMENTS

| | | | |
|---|---|---|---|
| 7,061,891 B1 * | 6/2006 | Kilfoyle | H04B 7/2606 370/335 |
| 8,515,777 B1 * | 8/2013 | Rajasenan | G16H 50/30 705/7.14 |

(Continued)

FOREIGN PATENT DOCUMENTS

KR 101693429 B1 1/2017

OTHER PUBLICATIONS

CoachAccountable—Software that makes your coaching better; obtained from the Internet Aug. 6, 2020; www.coachaccountable.com; 9 pages.

(Continued)

*Primary Examiner* — Evangeline Barr
*Assistant Examiner* — Jordan L Jackson
(74) *Attorney, Agent, or Firm* — Perkins Coie LLP

(57) ABSTRACT

A computer-implemented method for dynamically reallocating resources to users of a coaching service. The method can include initially allocating resources to users of the coaching service, receiving indications of activities of the users relative to their allocated resources, and comparing the activities relative to a reference value to produce an outcome including a likelihood that a target user will benefit from a target resource. Upon identifying the target user, a dynamic reallocation process deallocates the target resource from another user and reallocates the target resource to the target user.

21 Claims, 6 Drawing Sheets

(51) Int. Cl.
   *G09B 5/14*         (2006.01)
   *G16H 50/30*      (2018.01)
   *G09B 5/12*         (2006.01)
   *G16H 20/30*      (2018.01)

(56) References Cited

U.S. PATENT DOCUMENTS

| | | | |
|---|---|---|---|
| 2006/0053035 A1* | 3/2006 | Eisenberg | G16H 40/20 705/2 |
| 2007/0122780 A1 | 5/2007 | Moon et al. | |
| 2009/0137298 A1 | 5/2009 | Bedingfield et al. | |
| 2010/0312581 A1* | 12/2010 | Wachtell | G16H 40/20 707/812 |
| 2014/0108034 A1* | 4/2014 | Akbay | G06Q 10/06315 705/2 |
| 2014/0248595 A1* | 9/2014 | Crabtree | G09B 5/08 434/247 |
| 2014/0372133 A1* | 12/2014 | Austrum | G16H 50/30 705/2 |
| 2015/0341503 A1* | 11/2015 | Chandramouli | H04M 15/58 455/405 |
| 2017/0116379 A1* | 4/2017 | Scott | G16B 50/00 |
| 2017/0177808 A1* | 6/2017 | Irwin | G06Q 40/123 |
| 2018/0108272 A1* | 4/2018 | Ahmad | G16H 50/70 |
| 2018/0315499 A1* | 11/2018 | Appelbaum | G16H 20/30 |
| 2019/0304595 A1* | 10/2019 | Bergman | G06Q 10/06315 |
| 2019/0328290 A1* | 10/2019 | Dias | G16H 20/17 |
| 2020/0066397 A1* | 2/2020 | Rai | G06N 20/00 |

OTHER PUBLICATIONS

Insala Coaching Software; obtained from the Internet Aug. 6, 2020; www.insala.com/coaching-solutions.asp; 4 pages.

Nudge: Create your coaching app; https://nudgecoach.com/; obtained from the Internet Aug. 6, 2020; 5 pages.

* cited by examiner

DYNAMIC AND TARGETED ALLOCATION OF RESOURCES FOR COACHING SERVICE

CROSS-REFERENCE TO RELATED APPLICATION

This application claims priority to U.S. provisional patent application Ser. No. 62/884,981 titled "Dynamic and Targeted Allocation of Coaching Resources," filed Aug. 9, 2019, which is incorporated by reference herein in its entirety.

TECHNICAL FIELD

This disclosure generally relates to scaling a service that has limited resources, and more specifically, to techniques for scaling a service with limited resources in a specialized environment, such as for resources in a coaching service.

BACKGROUND

Coaching is a form of development in which a coach supports a client in achieving a goal by providing training and/or guidance. An effective coaching service utilizes resources including coaches, network and communication resources, and devices. A recipient benefits from having access to all available coaching resources. However, as the number of recipients increases, scaling a coaching service becomes complex and problematic. Specifically, the individual and collective costs for resources is relatively expensive, which limits the resources available for any coaching service.

For example, in diabetes management, a coaching service may be prescribed by a doctor for a patient to augment the patient's malfunctioning physiology. A doctor considers numerous factors to formulate a personalized diabetes management program. For example, blood glucose levels (BGLs), adverse effects of insulin, cost, the likelihood of patient adherence, and quality of life may be considered when choosing a disease management strategy for a patient.

The health status of a patient may change naturally or because of mismanagement due to the tedious and burdensome process required to adhere to a diabetes management program. As such, the patient risks experiencing diabetes-related complications. A coaching service can help a patient manage diabetes with ongoing treatment. For example, a coaching service can help a patient follow a rigid schedule to manage his or her diabetes with ongoing interactions through a smartphone. However, the availability of coaching services becomes scarce as the number of patients increases or the amount of resources decreases such that coaching services are ineffective for treating patients.

BRIEF DESCRIPTION OF THE DRAWINGS

Various features and parameters of the disclosed technology will become more apparent to those skilled in the art from a study of the Detailed Description in conjunction with the drawings. Embodiments of the disclosed technology are illustrated by way of example and not limitation in the drawings, in which like references indicate similar elements.

Figure 1:
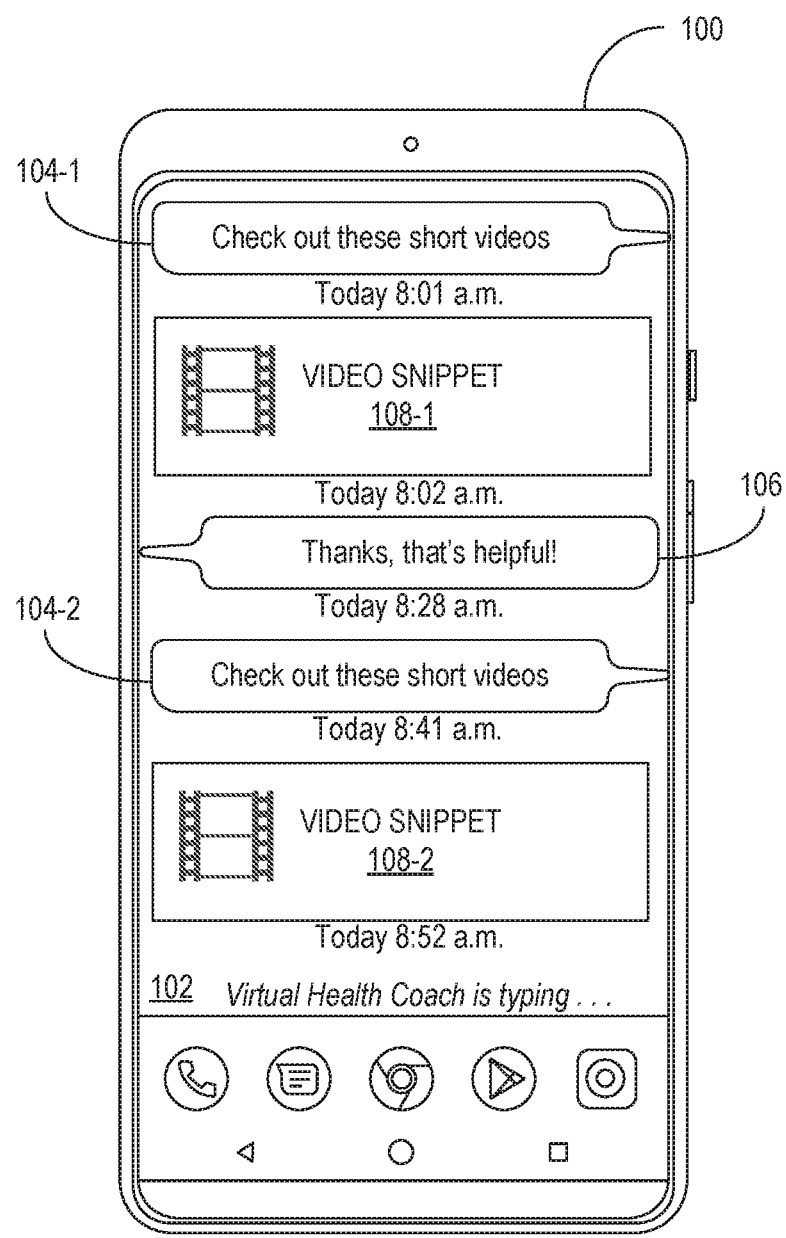
FIG. 1 illustrates a communication exchange on a computing device between a virtual coach and a patient.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

The disclosed embodiments address the problem of scaling virtual coaching services, which involves costly and limited resources. The solution involves a technique for reallocating resources (e.g., personnel, their available time, deployment of monitoring devices) based on who is likely to utilize and benefit from using the resources. The embodiments identify individual coaching recipients based on individual considerations and collective considerations of users of the virtual coaching service. For example, the embodiments may involve ranking or prioritizing coaching recipients and dynamically adjusting an allocation of resources based on current feedback from users or of the resources.

To aid in understanding, the disclosed embodiments describe an improved coaching service for diabetes management. However, the disclosed technology can be applied to any coaching service or any service that allocates resources. A diabetes management program can include a combination of a prescription for medications and a coaching service for aiding a patient to achieve a goal. For example, a doctor can conduct a survey to assess a patient's lifestyle and administer tests to determine a running average of blood glucose levels (BGLs). In combination with other factors, a coaching service can formulate a diabetes management program to deploy a coaching service.

A coaching service may include a combination of one-on-one coaching sessions for selected time increments, an allocation of content (e.g., videos, audio lectures), and the deployment of medical devices. The patient may be given treatments updated with the active assistance of a virtual coach. The burdensome nature of this form of coaching increases the risk that patients will simply quit, thereby increasing the likelihood of non-adherence which is substantially more dangerous than just quitting any coaching program.

To overcome these drawbacks, embodiments of a coaching service for diabetes management can vary the types and amounts of resources allocated to a patient for the individual patient and among a group of patients. In some embodiments, the disclosed coaching service is a computer-implemented technology that can help patients manage diabetes. For example, a mobile application ("app") for self-managing diabetes may include a coaching algorithm such as a chatbot implemented as a virtual or simulated coach. Virtual coaching involves the use of an automated communication device or service such as a chatbot that can engage a patient with a simulated conversation via a messaging mechanism of a mobile portal or web-based portal on a routine or regular basis.

In some embodiments, a coaching service can collect physiological and contextual information of patient activity (e.g., metabolic activity/exercise or consuming medication, eating of particular diet, real-time health/activity state from mobile/wearable sensors, self-reported health/activity state), external factors (e.g., longer daylight, average temperature, season, geographical altitude, pollution level, environmental state from mobile/wearable sensors), or patient profile information (e.g., age, gender, genotype or phenotype information) to improve a content selection algorithm or adjust determined results.

The coaching service can adapt an allocation of coaching resources based on the collective needs of patients. For example, patients can be categorized into different buckets based on the urgency of their needs. Patients with more critical medical conditions can have a greater portion of the total resources allocated to them compared to patients that have more manageable medical conditions. Moreover, the allocation of resources can dynamically change to adapt to circumstances of each individual participating in a coaching service based on information obtained from various sources such as electronic medical records (EMRs), pharmacy data, self-reported information, and monitored data such as that obtained from a continuous glucose monitor (CGM). Hence, coaching resources can have an initial allocation that is mapped in different combinations to different coaching recipients depending on ongoing changes in the needs of coaching recipients based on current information.

When the resources are distributed, the coaching service can monitor each patient's interactions with a particular resource and swap resources to maintain the patient's engagement in the coaching service. In another example, when a virtual coach chooses to allocate a resource to a particular patient, the coaching service can intervene to prompt the virtual coach with a suggested action based on the individual patient or collective needs of all the coach's patients. For example, a virtual coach might intuitively decide to allocate more one-on-one time to a patient that is not responding to electronic messages from the coach. The coaching service can redirect the virtual coach to allocate more time to another patient that historically utilizes and benefits more from one-on-one time.

As used herein, a "coach" or "virtual coach" may refer to a computer-implemented technique for automating at least some aspect of a coaching process via a computing device that encourages a user of the computing device to adhere to a given protocol in order to achieve a goal of that protocol. In one example, a virtual coach is an implementation of a chatbot or any automated or semi-automated communications mechanism or device that can communicate with a patient via a local or network portal. In another example, a virtual coach is a human that uses a computing device to communicate with individuals of a coaching service.

In some embodiments, a virtual coach could be completely automated to function like a human being. As such, the user of a computing device can engage in a simulated natural conversation with a virtual coach. In some embodiments, a virtual coach operates in accordance with a set of rules that are customized for a particular user, a particular type of user, a group of users, etc. In another example, a virtual coach could be partially automated such that a user could influence the way a virtual coach operates live (e.g., in real-time or near real-time) while engaged with a user.

As used herein, a "user" may refer to an individual or entity that interacts with a coaching service via a computing device. For example, a user includes a coaching recipient such as a diabetic patient that can manage his or her diabetes with a virtual coaching service by consuming content. In another example, a user is a virtual coach that interacts with a patient over a coaching platform to virtually coach the patient.

As used herein, the term "dynamic" may refer to an allocation of resources that is affected by the passage of time. For example, dynamically allocated resources are selected while a user is engaged in a coaching service (e.g., in real-time or near real-time). The allocation of resources or an expected deployment could be changed depending on current activity data (e.g., obtained from sensors). Hence, the disclosed embodiments improve over using historical clinical visit data by considering day-to-day behavioral characteristics and real-time sensor data. In some embodiments, reoccurring polling of one or more patients could be implemented to adjust resource allocation. Further, the disclosed embodiments could rank/prioritize resources/patients throughout an entire population or in distinct buckets of patients (e.g., groups of patients bucketized by location, payment schemes).

As used herein, a "resource" may refer to any resource of a coaching service. An example of a resource is a time increment of the total time that a virtual coach has available to coaching recipients. Another example includes access to computing or network devices such as communications devices with messaging features. Yet another example of a resource is a medical device such as a CGM.

A coaching service can adapt an allocation of coaching resources based on the individual needs of a patient. For example, coaching to treat chronic diseases like diabetes may involve routine interactions between a virtual coach and a patient over communications channels such as text or video chat channels and deployment of a medical device (e.g., CGM). As the number of patients with similar needs increases, the scarcity of resources limits the ability of effectively coaching all the patients at the same time.

In some embodiments, a coaching service can dynamically recommend a reallocation of resources to a virtual coach of multiple patients. The recommended reallocation could be formulated based on data obtained about one or more of the coach's patients. In some embodiments, the patients are ranked to facilitate allocation by the coach. As such, the coaching service can improve a patient's experience by guiding the patient's virtual coach to maintain effective and timely services that maintain each patient's engagement to complete coaching exercises. Hence, the disclosed coaching service is more effective from the perspective of participants, coaches, and in terms of reducing the demand on resources.

In some embodiments, coaching resources are selected dynamically in real-time or near real-time to enable active adaptation to recent data pulled from different sources. The resources are allocated to patients and/or a virtual coach to improve the coach/user relationship. The coaching service can dynamically swap resources among patients as a patient advances or regresses in a coaching protocol (e.g., program). As such, a resource allocation changes to adapt to individual and collective needs as determined based on data obtained from various sources. The coaching service can also sort or rank resources and prioritize patients to rapidly adapt to changing circumstances of the patients.

The frequency of the decision to dynamically change content can vary depending on the availability of data on which the decision is based. For example, a refresh rate to reallocate resources of a coaching session can occur rapidly if based on data obtained from a continuous monitoring device. Moreover, the coaching service can throttle a frequency for one patient when other patients have a greater need for a resource.

A virtual coaching service includes a technical means such as a platform that administers network portals for users to access content for coaching sessions over a medium such as a communications network. In the context of a diabetes management program, a health-related electronic coaching tool can include an ordered structure of available resources to guide a diabetic patient to maintain eating habits in a step-by-step manner. For example, a patient may be granted more time for one-on-one coaching at the beginning of a disease management program. The one-on-one coaching tapers off as the patient progresses through the program and a playlist of audio recordings can be gradually introduced to keep the patient engaged in the program. A coaching service may include different resources for different categories of patients to achieve goals. The availability of resources may be pre-arranged before a patient begins a coaching session. A combination of resources is initially selected based on factors including the patient's demographic profile, historical information, input from other users of the coaching service, etc. For example, an initial set of resources for young adults can differ from resources for older adults.

A virtual coaching service can recommend a reallocation of resources for a virtual coach as a function of a combination of factors including, for each of the coach's patients, a patient profile, physiological data (e.g., real-time glucose data), patient's selections, historical recommended actions and/or compliance with the actions, and other patient activity patterns with similar profiles (e.g., demographic, disease profile, lab values, medication list, and clinical data). The reallocation can effectively ration limited resources to improve the overall effectiveness of the coach's services. In some embodiments, an allocation of a first resource for a first patient is weighted more heavily compared to a second patient or a second resource based on how the first or second patients currently utilize or have historically utilized resources. For example, a medical device that is not being actively utilized by a patient may be reallocated to another patient that has historically utilized that or any other resource.

In one example, a coaching service can initially allocate resources to a pool of patients that are assigned to the same virtual coach. For example, the coaching service can populate a library of coaching resources with a coach's profile including time availability, network and computing resources such as communications devices, and medical devices such as glucose monitors. The resources can be initially distributed equally among the coach's patients or unequally based on each patient's individual needs in accordance with an individual coaching protocol (e.g., strategy).

The reallocation of resources increases the flexibility and variability to adapt to the needs of patients. For example, a segment for diabetes management may include a 60-minute audio lecture that is burdensome for a patient to consume. By dividing the 60-minute audio segment into several shorter snippets, patients can listen to different combinations of the snippets over an extended period. Thus, content resources can be modified and reallocated to patients based on their individual needs and the effectiveness of a particular resource for advancing the individual towards their goals. Further, the disclosed embodiments can pinpoint a patient or combination of resources that have a greater likelihood of improving the effectiveness of coaching.

A virtual coach can use a messaging mechanism to improve engagement with a patient and to communicate various forms of content. Examples of a messenger mechanism include a chat messenger, SMS text, or other input mechanisms that can be used to increase engagement by sharing educational content. In some embodiments, a virtual coach can engage a user in a conversation on a computing device and identify effective content objects for the patient.

For example, FIG. 1 illustrates a communication exchange on a smartphone between a virtual coach and a patient. The communication exchange is between a patient using a computing device 100 and the patient's virtual coach during an active coaching session. The virtual coach service can allocate resources while being engaged in an SMS text conversation. As illustrated, the computing device 100 is a smartphone with a messaging portal 102 that includes comments from the virtual coach 104-1 and 104-2 and the patient 106 engaged in a conversation. Although embodied on a smartphone, the messaging portal 102 can run on any computing device that allows the user to obtain content objects which, in this example, are linked video snippets 108-1 and 108-2. The messaging portal 102 can be included in an app or be part of an operating system (OS) of a smartphone or other computing device. The messaging portal 102 can receive messages from the virtual coach to prompt the patient's device to render content objects. In this example, the virtual coach shares links to video snippets 108-1 and 108-2 to help the patient learn to manage a disease. The communication of content objects can vary by frequency, type, and the amount needed to achieve the desired outcome.

Figure 2:
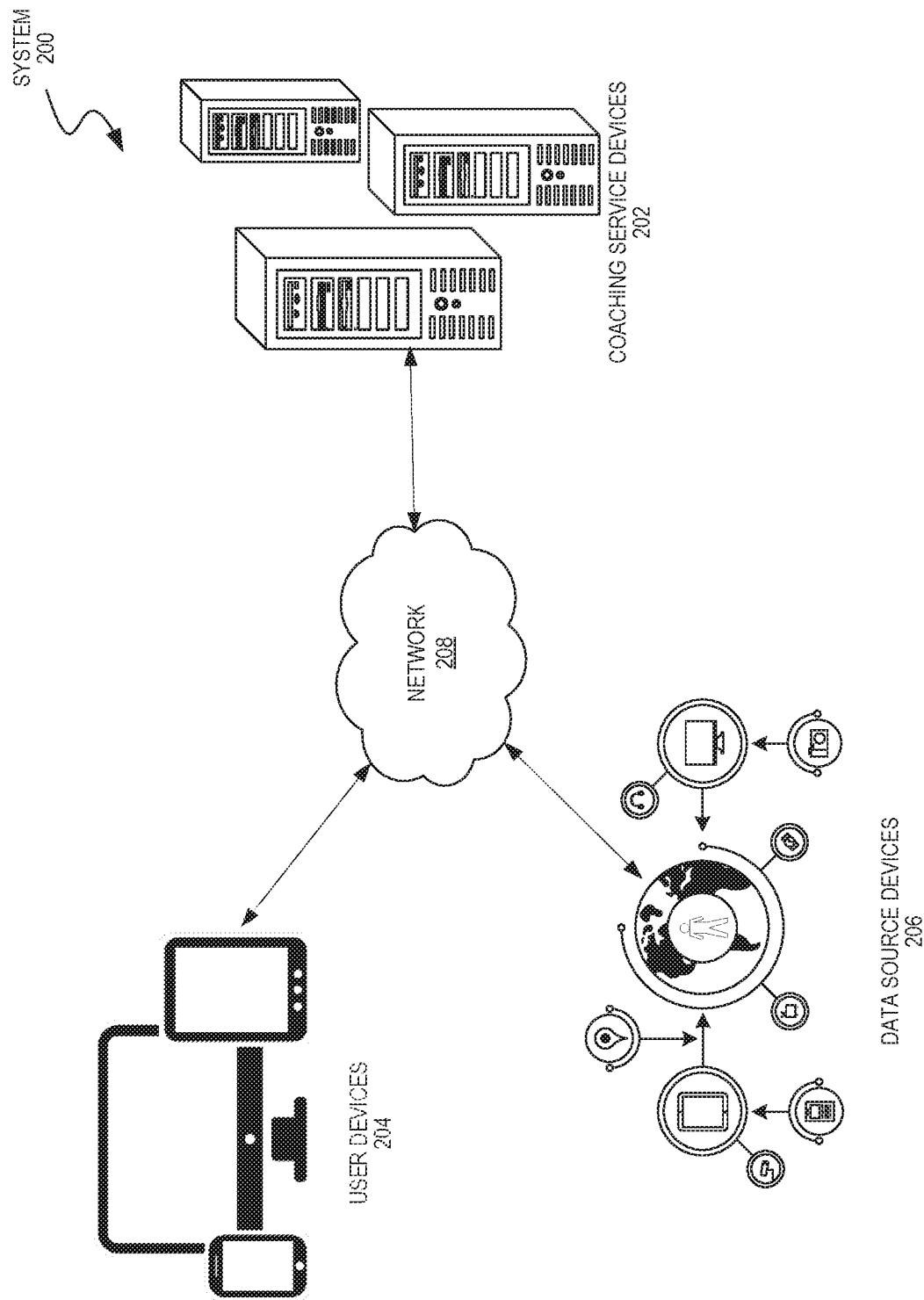
FIG. 2 is a block diagram that illustrates a system that implements a coaching service.

FIG. 2 is a block diagram that illustrates a system 200 that can implement a coaching service. The system 200 can dynamically reallocate resources of the coaching service. The system 200 includes components such as coaching service devices 202 that run a dynamic resource allocation engine, communications user devices 204 (also referred to individually as a user device 204), and data source devices 206 that collect information used to dynamically change a resource allocation for an individual user or among a group of users. The components are all interconnected over a communications network 208 ("network 208") such as the Internet.

From the perspective of the user devices 204, resources are dynamically selected and presented for one-on-one coaching. An example includes coaching content (e.g., videos) that are rendered on a display device of the user devices 204. In another example, physiological monitoring devices are resources that are worn by users and can communicate physiological data to the user devices 204 over short-range radio connections (e.g., Bluetooth), which can relay the physiological data about users over the network 208 to the coaching service devices 202 in accordance with coaching protocols. For example, a media resource can be pre-selected from among multiple media resources and scheduled for rendering by a user device 204 at a selected position in the series of media resources. Rather than rendering the resource that was pre-selected for the series, a substitute resource can be selected in response to information collected in real time or near-real time from different monitoring device and schedule to render in accordance with the user's coaching protocol.

From the perspective of the coaching service devices 202, the coaching service is administered to enable coaching through the user devices 204 by one or more virtual coaches. Each user can access the coaching service over the user devices 204. The coaching service devices 202 can authorize each user device 204 to access a resource in accordance with a respective coaching protocol for each user. The coaching service can then dynamically select a respective next resource for each user. The coaching service devices 202 can authorize or restrict access to a next resource for each of the user devices 204 in accordance with the coaching protocol for that user.

The network 208 may include any combination of private, public, wired, or wireless portions. The data or information communicated over the network 208 may be encrypted or unencrypted at various locations or along different portions of the network 208. Each component of the system 200 may include combinations of hardware and/or software to process data or information, perform functions, communicate over the network 208, and the like. For example, any component of the system 200 may include a processor, memory or storage, a network transceiver, a display, OS and application software (e.g., for providing a user interface), and the like. Other components, hardware, and/or software included in the system 200 that would be well known to persons skilled in the art are not shown or discussed herein for the sake of brevity.

The user devices 204 can be any communications device that is used to interact with the system 200. Examples of user devices 204 include smartphones (e.g., APPLE IPHONE, SAMSUNG GALAXY, NOKIA LUMINA), tablet computers (e.g., APPLE IPAD, MICROSOFT SURFACE), computers (e.g., APPLE MACBOOK, LENOVO THINKPAD), and any other device that is capable of exchanging data with the coaching service devices 202 over the network 208.

The coaching service devices 202 can execute a coaching service on any number of server computers that can operate a dynamic resource allocation engine. The coaching service devices 202 can store algorithms to dynamically reallocate resources of a coaching service. For example, an algorithm may include a combination of rules for determining whether a resource allocated to one coaching recipient should be reallocated to a different coaching recipient.

The data source devices 206 may include any number of servers or other computing resources that can collect, store, and/or provide data or information related to coaching recipient, virtual coaches, or resources for the coaching service devices 202 for use in determining whether to reallocate resources. The data source devices 206 may include any source of healthcare-related information. For example, the data source devices 206 may include any providers such as medical facilities, private offices, or devices administered by healthcare professionals. In some embodiments, the data or information may include at least portions of medical records.

Figure 3:
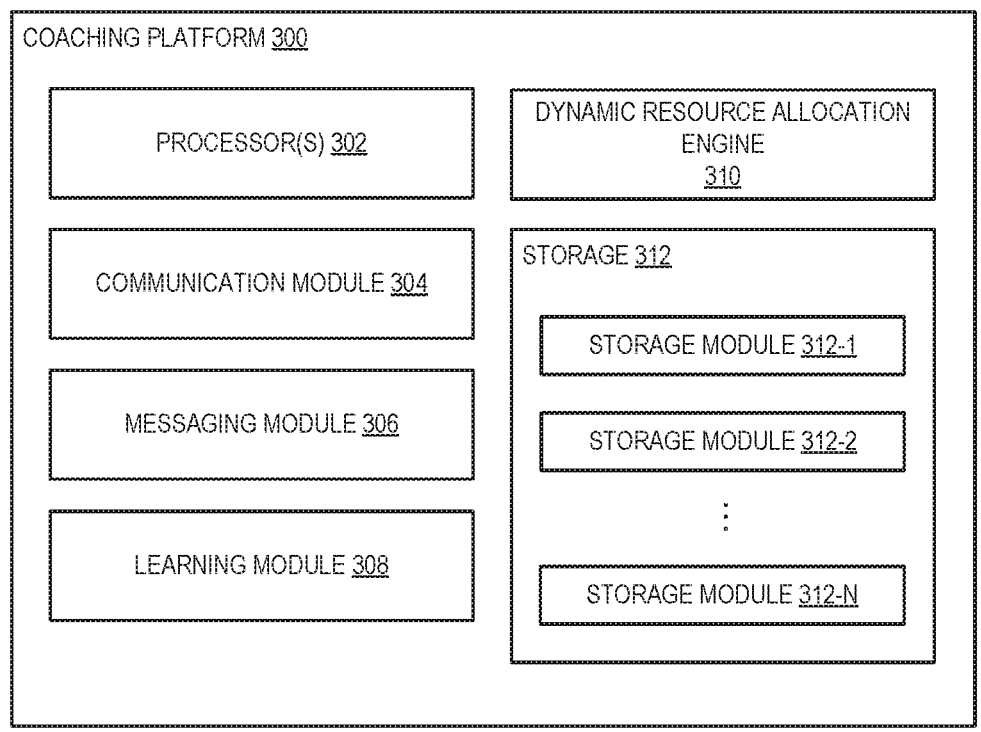
FIG. 3 is a block diagram that illustrates functional components of a coaching service.

FIG. 3 is a block diagram that illustrates functional components of a coaching service. A coaching platform 300 ("platform 300") can include components or modules that collectively operate to perform a process for a coaching service. As used herein, a "component" or "module" may refer to a part or independent unit of hardware and/or software that performs one or more distinct functions. In some instances, a module is self-contained, separable, and/or interchangeable relative to other modules.

As shown, the platform 300 includes one or more processors 302, a communication module 304, a messaging module 306, a learning module 308, a dynamic resource allocation engine 310, and storage 312 ("storage modules 312"). Embodiments of the platform 300 may include some or all of these modules or components, along with other modules and/or components that are within the scope of the disclosure or known to persons skilled in the art but not shown herein for the sake of brevity.

The processor(s) 302 can execute modules from instructions stored in the storage modules 312, which can be any computing device or mechanism capable of storing information. The communication module 304 may manage communications among components of the platform 300 and/or between the platform 300 and another computing device. For example, the communication module 304 can facilitate communication of user inputs or contextual information related to a patient's coaching experience. The received inputs or information can be wirelessly uploaded by the user's computing device (e.g., the user computing device 204) or other devices (e.g., data source devices 206) over a network (e.g., network 208) to a server computer (e.g., coaching service devices 202).

The communication module 304 facilitates the exchange of communications between a user device and the dynamic resource allocation engine 310. Further, the communication module 304 may transmit search results to a computing device associated with a patient or the patient's coach. The user inputs or contextual information communicated over the communication module 304 can be stored in storage modules 312, one or more particular storage modules (e.g., storage modules 312-1 through 312-N), a remote storage accessible to the platform 300, or some combination thereof.

The messaging module 306 can generate a messaging interface that allows a coaching recipient to interact with a coaching service. The dynamic resource allocation engine 310 includes underlying logic that is executed to decide when and what resources to reallocate.

In some embodiments, user input, contextual information, and/or values extracted therefrom can be stored in the storage modules 312 along with the information used by the dynamic resource allocation engine 310. In this way, the dynamic resource allocation engine 310 can improve the allocation of resources for a coaching recipient or among coaching recipients.

In some embodiments, the learning module 308 can utilize the user inputs and/or contextual information to improve the coaching platform 300. For example, the learning module 308 can aggregate collected user inputs and contextual information from numerous users associated with numerous patients, and process those collected inputs or information in accordance with machine-learning algorithms to train the dynamic resource allocation engine 310. Examples of machine learning algorithms/techniques include Naïve Bayes Classifier algorithms, K Means Clustering algorithms, Support Vector Machine algorithms, linear regression, logic regression, and artificial neural networks.

The coaching platform 300 can also collect contextual information (e.g., real-time health/activity state from mobile/wearable sensors, self-reported health/activity state, environmental state from mobile/wearable sensors) to help or improve the resource allocation algorithm. Although not shown or described herein for the sake of brevity, the coaching platform 300 includes modules that ensure compliance with privacy settings and data security.

Figure 4:
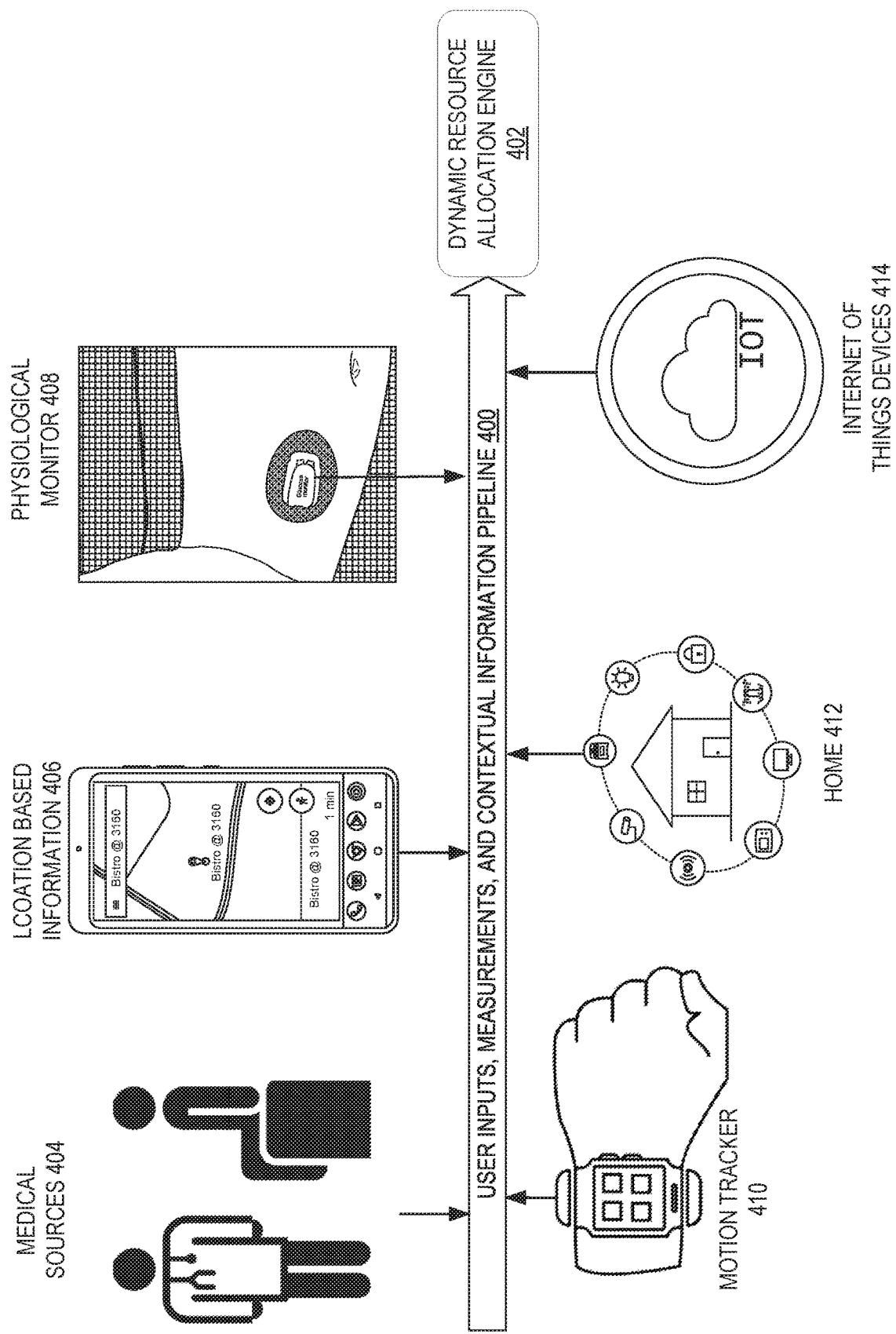
FIG. 4 is a block diagram that illustrates an information pipeline for a dynamic resource allocation engine.

FIG. 4 is a block diagram that illustrates an information pipeline 400 that communicates data from various sources to a dynamic resource allocation engine 402, which can dynamically change or recommend a change in the allocation of resources based on the collected data. The pipeline 400 obtains data and information from various diverse sources for the dynamic engine. The pipeline 400 represents one or more communication channels (e.g., network 208) and devices (e.g., user devices 204 or data source devices 206).

Examples of the diverse sources (e.g., data source devices 206) illustrated in FIG. 4 include medical sources 404, a patient's location information 406, a physiological monitor 408, a motion tracker 410, monitoring devices at the patient's home 412, and virtually any other computing devices such as internet of things (IoT) devices 414 that can communicate useful information for the dynamic resource allocation engine 402.

For example, medical sources 404 can include EMRs that describe a patient's medical history and prescriptions. Examples of the medical sources 404 include hospitals, clinics, pharmacies, or the patients or medical providers themselves. For example, a patient can input medical information into an application on a mobile phone when engaged in a discussion with a virtual coach about diabetes management. In addition to the user inputs provided by the user of a computing device, contextual information can be derived from conversations during a coaching session. The medical information can include utilization data that indicates how often a patient sought medical assistance or experienced an emergency. Other examples of the medical sources 404 include patient-reported data of surveys or response patterns from other similarly situated patients.

Examples of location information 406 include a patient's location, which could be determined by the GPS receiver of the patient's smartphone. The location information 406 can be used to determine, for example, whether the patient visited a restaurant or a gym. If so, a virtual coach can engage the patient to obtain more details about what the user ate at the restaurant or the exercise that the patient participated in while at the gym. This contextual information can be used by the dynamic resource allocation engine 402 to determine whether a reallocation of resources is required and the degree of the change necessary to manage diabetes.

An example of the physiological monitor 408 is CGM that can continuously collect BGLs of a patient. The physiological monitor 408 can be worn by the patient to monitor a physiological parameter of the patient on a regular basis, continuously throughout the day. Any physiological monitoring device that collects physiological parameter values that are indicative of a disease or useful for managing a disease could be used by the dynamic resource allocation engine 402 to determine whether a reallocation of resources is required and to determine the degree of the required change.

Examples of contextual information from the motion tracker 410 could include data or information about the user's activities such as whether the user is exercising, the duration and rigor of the exercise, and related physiological indicators of the user such as heart rate. This fitness information can be used alone or in combination with other contextual information to influence the outcome of the dynamic resource allocation engine 402.

Examples of contextual information obtained by monitoring the patient's home 412 can include intelligent appliances that monitor the user's activities. For example, a smart refrigerator can detect the frequency that a patient opens the refrigerator and alert the dynamic resource allocation engine 402 to change a resource allocation in response to this activity. In another example, the home 412 can include a virtual assistant such as the AMAZON ECHO or GOOGLE HOME, which use natural language processing to match user text and voice inputs to execute commands.

Examples of the IoT devices 414 include any computing devices with sensors that can capture contextual information (e.g., environmental sensors) and that can connect over a network to the dynamic resource allocation engine 402. The examples shown in FIG. 4 are not meant to be limiting. Rather, the dynamic resource allocation engine 402 can process user inputs or contextual information from any device capable of generating or capturing the inputs or contextual information and communicating it to the dynamic resource allocation engine 402.

In some embodiments, user inputs or contextual information can be collected by the pipeline 400 continuously (e.g., periodically, hourly, daily) or on demand. For example, a virtual coaching service can administer a messaging portal that engages a patient in simulated conversations periodically to receive inputs. The user inputs or contextual information may indicate an ongoing severity of symptoms experienced by the patient. In some embodiments, these user inputs and contextual information can be used to update the patient's profile.

In some embodiments, user inputs or contextual information can be used for compliance monitoring. For example, a mobile app may prompt the user to input whether the patient is complying with a desired behavior, such as regularly exercising. Tracking a patient's compliance in combination with data about the patient's outcomes can be used to determine whether a resource for diabetes management is effective at managing the patient's diabetes.

Figure 5:
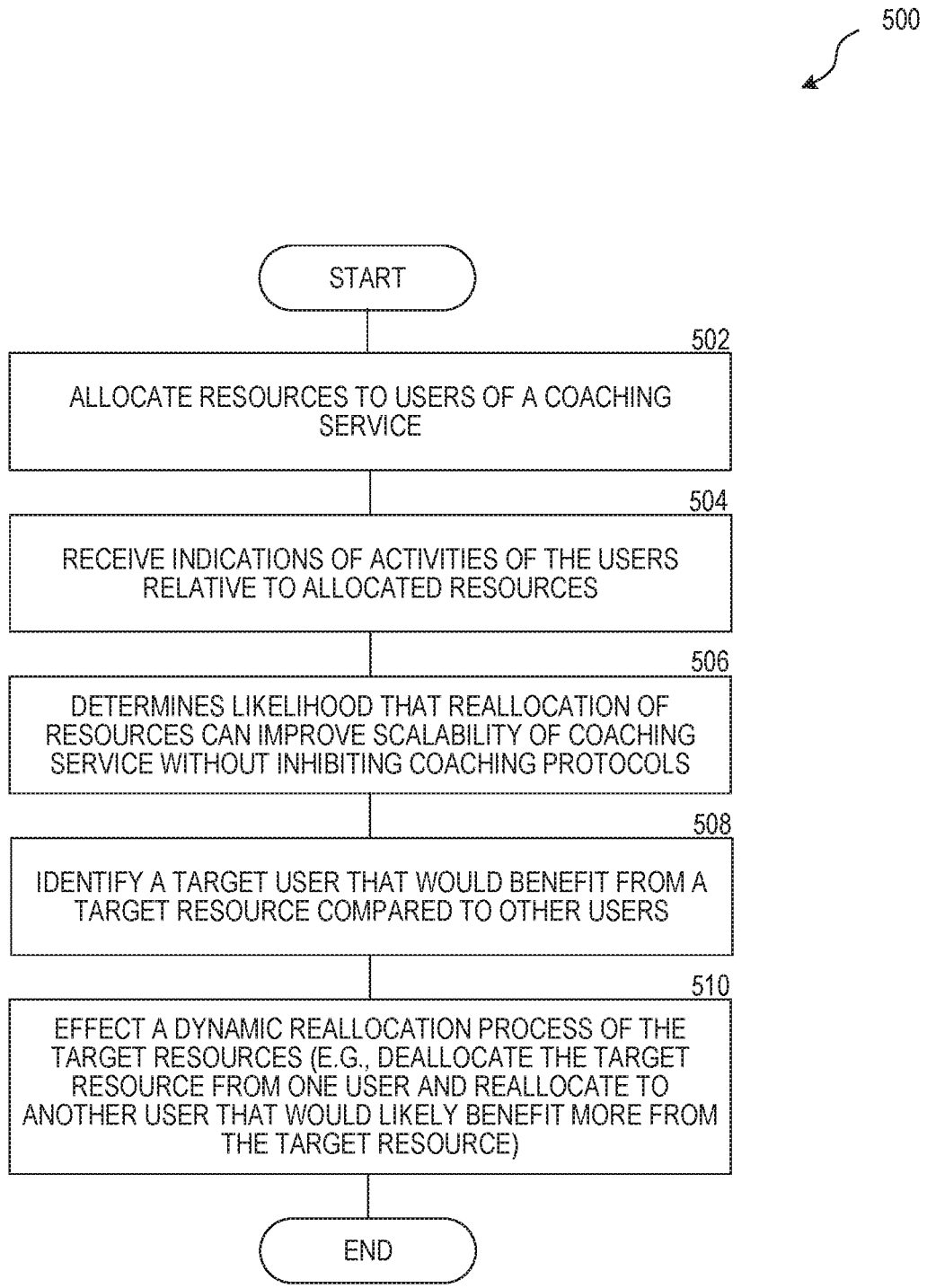
FIG. 5 is a flow diagram that illustrates a method for dynamically reallocating resources of a coaching service.

FIG. 5 is a flow diagram that illustrates a method for dynamically allocating resources of a coaching service. An example of a coaching service is a disease management service with a coaching component for patients. Examples of different types of resources include a time for personalized coaching, a medical device, a computing device, or content objects. A pool of resources can include the same or different types of resources.

At 502, the coaching service allocates a pool of resources for users (e.g., coaching recipients, virtual coaches) of the coaching service for access over a communications network. The pool of resources is initially allocated in accordance with a respective coaching protocol of each coaching recipient. For example, a coaching recipient can be a diabetic patient and a coaching protocol can be for diabetes management including weight management.

At least some of the coaching recipients can share a common virtual coach, which is a type of limited resource. Each user participates in the coaching service through communication devices such as a computer, smartphone, smartwatch, etc. For example, a first resource can include a first time increment for coaching by the virtual coach and a second resource can include a second time increment for coaching by the same virtual coach.

At 504, the coaching service receives indications of activities by the coaching recipients relative to allocated resources. For example, the coaching service can receive a first indication of a first activity of a first user relative to a first resource and receive a second indication of a second activity of a second user relative to a second resource. The first and second coaching recipients had resources initially allocated to them based on their respective coaching protocols. For example, the first activity can be a utilization amount of a first time increment by the first coaching recipient and the second activity can be a utilization amount of a second time increment by the second coaching recipient.

In some embodiments, an activity includes measurements obtained by a sensor worn by a coaching recipient such as a BGL obtained by a CGM. In some embodiments, the indication is a historical measure of utilization of any resources by a user or a measure of progress of a coaching protocol during a time increment when a user was allocated resources. In some embodiments, an activity includes an input from a user that is responsive to a reoccurring polling process by the coaching service. For example, the coaching service can poll users about a perceived effectiveness of an allocated resource.

At 506, the coaching service determines a likelihood that a reallocation of resources can improve scalability of the coaching service over the communications network without inhibiting existing coaching protocols. In one example, the coaching service compares activities relative to a reference value to produce an outcome including a likelihood that users will advance in their respective coaching protocol with an allocated resource. An example of the reference value is a threshold utilization value for a resource. The coaching service authorized each user to access a virtual coach over a network on communication devices during an allocated time increment.

At 508, the coaching service identifies a target user that can utilize a target resource that is currently allocated to another user and where reallocation to the target user can improve scalability of the coaching service without affecting the target user's progress in the coaching protocol. For example, a target user can be identified as having a historically higher utilization rate of resources compared to other users. In another example, the target user is identified based on an activity profile for the user that is maintained by the coaching service. In another example, the target user was not allocated a resource as a result of the initial allocation but is deemed later to potentially benefit from a resource.

In another example, a target user is a patient that is identified based on at least one of a medical claim data, an ongoing physiological measurement, or ongoing sensor data. In another example, a target user is identified based on standard clinical data, a prescription profile, a risk profile including metric (e.g., a health risk score) based on amount or frequency of healthcare related events, and/or a self-identified measure of confidence to manage a disease. In yet another example, a target user is identified based on an activity profile of the patient including a level of engagement with the coaching service over a selected time increment.

At 510, the coaching service effects a dynamic reallocation process of resources among the users based on the outcome of the comparison at 506. The dynamic reallocation process can include reallocating of a portion of the of an allocated time increment when the amount of utilization by a user is less than the amount of utilization of another time increment by another user. Hence, the coaching service can deallocate a resource from one user and reallocate the deallocated resource to a target user.

In one example, deallocating at least a portion of the target resource includes throttling use or intensity of a medical service based on real-time or near real-time monitoring of a physiological parameter. For example, a CGM may be reallocated from one patient to another patient and the original user may be instructed by a virtual coach over a communications device to begin a routine finger-pricking test once per day. In some embodiments, the reallocation is based on a unique factor of the target patient, sensor data associated with the target patient, an availability of a resource, or a global factor of the plurality of patients.

The dynamic reallocation process may assist a virtual coach itself in reallocating resources. For example, the process may include ranking resources based on a measure of availability or criticality for addressing a health issue. The coaching service can prioritize users based on a measure of effective utilization of resources, and then recommend a reallocation of the resources among the users based on the ranking of the resources and the prioritization of the users. In another example, a set of resources are presented to the coach. The set of resources are available for reallocation. The coaching service receives an indication that the virtual coach selected a resource for the target user.

In some embodiments, the dynamic reallocation process operates on groups of users. For example, users can be separated into buckets that are associated with a respective characteristic that is common to all users of a bucket. For example, all the users of one bucket may be managing their diabetes with a coaching service. Another bucket may be associated with a particular demographic of users such as an age range. In yet another example, the characteristic is a geographic location or a payment program of the coaching service. As such, resources can be allocated on a per-bucket basis.

Figure 6:
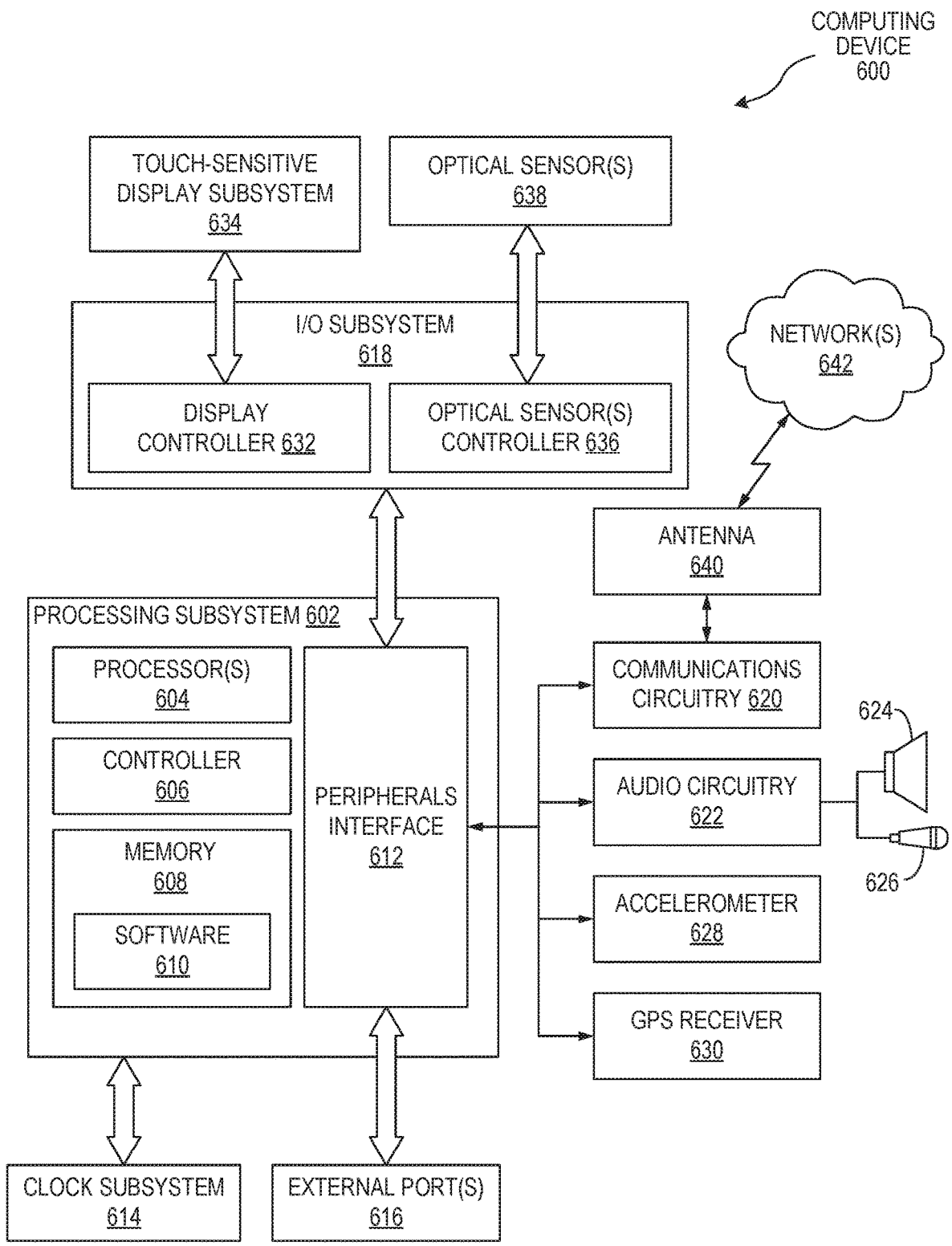
FIG. 6 is a block diagram that illustrates an example computing device in which aspects of the disclosed technology can be embodied.

FIG. 6 is a block diagram that illustrates an example computing device (e.g., computing device 100) in which aspects of the disclosed technology can be embodied. For example, the coaching platform 300 of FIG. 3 may be hosted on the computing device 600. The computing device 600 may include generic components and/or components specifically designed to carry out the disclosed technology. The computing device 600 may be a standalone device or part of a distributed system (e.g., system 200 of FIG. 2) that spans networks, locations, machines, or combinations thereof. For example, components of the computing device 600 may be included in or coupled to a system-on-chip (SOC), a single-board computer (SBC) system, a desktop or laptop computer, a kiosk, a mainframe, a mesh of computer systems, or combinations thereof.

In some embodiments, the computing device 600 can operate as a server device or a client device in a client-server network environment, or as a peer machine in a peer-to-peer system. In some embodiments, the computing device 600 may perform one or more steps of the disclosed embodiments in real-time, near real-time, offline, by batch processing, or combinations thereof.

The computing device 600 includes a processing subsystem 602 that includes one or more processors 604 (e.g., central processing units (CPUs), application specific integrated circuits (ASICs), and/or field programmable gate arrays (FPGAs)), a memory controller 606, memory 608 that can store software 610, and a peripherals interface 612. The memory 608 may include volatile memory (e.g., random-access memory (RAM)) and/or non-volatile memory (e.g., read-only memory (ROM)). The memory 608 can be local, remote, or distributed. The computing device 600 can also include a clock subsystem 614 that controls a timer for use in some embodiments. The components of the computing device 600 are interconnected over a bus (not shown) operable to transfer data between hardware components.

The peripherals interface 612 is coupled to one or more external ports 616 which can connect to an external power source, for example. The peripherals interface 612 is also coupled to an I/O subsystem 618. Other components coupled to the peripherals interface 612 include communications circuitry 620, audio circuitry 622 for a speaker 624 and a microphone 626, an accelerometer 628, a GPS receiver 630 (or global navigation satellite system (GLONASS) or other global navigation system receiver), and other sensors (not shown). The GPS receiver 630 is operable to receive signals concerning the geographic location of the computing device 600. The accelerometer 628 can be operable to obtain information concerning the orientation (e.g., portrait or landscape) of the computing device 600.

The I/O subsystem 618 includes a display controller 632 operative to control a touch-sensitive display system 634, which further includes the touch-sensitive display of the computing device 600. The I/O subsystem 618 also includes an optical sensor(s) controller 636 for one or more optical sensors 638 of the computing device 600. The I/O subsystem 618 includes other components (not shown) to control physical buttons.

The communications circuitry 620 can configure the antenna 640 of the computing device 600. In some embodiments, the antenna 640 is structurally integrated with the computing device 600 (e.g., embedded in the housing or display screen) or coupled to the computing device 600 through the external ports 616. The communications circuitry 620 can convert electrical signals to/from electromagnetic signals that are communicated by the antenna 640 to networks 642 (e.g., network 208 of FIG. 2) or other devices. For example, the communications circuitry 620 can include radio frequency (RF) circuitry that processes RF signals communicated by the antenna 640.

The communications circuitry 620 can include circuitry for performing well-known functions such as an RF transceiver, one or more amplifiers, a tuner, oscillators, a digital signal processor, a CODEC chipset, a subscriber identity module (SIM card or eSIM), and so forth. The communications circuitry 620 may communicate wirelessly via the antenna 640 with the networks 642 (e.g., the Internet, an intranet and/or a wireless network, such as a cellular network, a wireless local area network (LAN) and/or a metropolitan area network (MAN)) or other devices.

The software 610 can include an OS software program, application software programs, and/or modules (e.g., the communication module 304, messaging module 306, learning module 308, dynamic resource allocation engine 310, storage modules 312 of FIG. 3). For example, a GPS module can determine the location of the computing device 600 based on the GPS signals received by the GPS receiver 630. The GPS module can provide this information to components of the computing device 600 for use in various applications (e.g., to provide location-based contextual information).

A software program, when referred to as "implemented in a computer-readable storage medium," includes computer-readable instructions stored in the memory (e.g., memory 608). A processor (e.g., processors 604) is "configured to execute a software program" when at least one value associated with the software program is stored in a register that is readable by the processor. In some embodiments, routines executed to implement the disclosed embodiments may be implemented as part of OS software (e.g., Microsoft Windows and Linux) or a specific software application, component, program, object, module, or sequence of instructions referred to as "computer programs."

Computer programs typically comprise one or more instructions set at various times in various memory devices of the computing device 600, which, when read and executed by the processor 604, will cause the computing device 600 to execute functions involving the disclosed embodiments. In some embodiments, a carrier containing the aforementioned computer program product is provided. The carrier is one of an electronic signal, an optical signal, a radio signal, or a non-transitory computer-readable storage medium (e.g., the memory 608).

Operation of the memory 608, such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

The computing device 600 may include other components that are not shown nor further discussed herein for the sake of brevity. One having ordinary skill in the art will understand any hardware and software that is included but not shown in FIG. 6. While embodiments have been described in the context of fully functioning computing devices, those skilled in the art will appreciate that the various embodiments are capable of being distributed as a program product in a variety of forms and that the disclosure applies equally, regardless of the particular type of machine or computer-readable media used to actually effect the embodiments.

REMARKS

The embodiments set forth above represent necessary information to enable those skilled in the art to practice the embodiments and illustrate the best mode of practicing the embodiments. Upon reading the following description in light of the accompanying Figures, those skilled in the art will understand the concepts of the disclosure and will recognize applications of these concepts that are not particularly addressed herein. It should be understood that these concepts and applications fall within the scope of the disclosure and the accompanying embodiments.

The purpose of the terminology used herein is only for describing embodiments and is not intended to limit the scope of the disclosure.

Reference to "one embodiment" or "an embodiment" means that a particular feature, structure, or parameter described in connection with the embodiment is included in at least one embodiment of the disclosure. The appearances of the phrase "in one embodiment" in this disclosure are not necessarily referring to the same embodiment, nor are separate or alternative embodiments necessarily mutually exclusive of other embodiments. Moreover, various features are described that may be exhibited by some embodiments and not by others. Similarly, various requirements are described that may be requirements for some embodiments and not for other embodiments.

As used herein, unless specifically stated otherwise, terms such as "processing," "computing," "calculating," "determining," "displaying," "generating," or the like, refer to actions or processes of an electronic device that manipulates and transforms data, represented as physical (electronic) quantities within the computer's memory or registers, into other data similarly represented as physical quantities within the device's memory, registers, or other such storage medium, transmission, or display devices.

When used in reference to a list of multiple items, the word "or" is intended to cover all of the following interpretations: any of the items in the list, all of the items in the list, and any combination of items in the list.

Unless the context clearly requires otherwise, throughout the description and the embodiments, the words "comprise," "comprising," and the like are to be construed in an inclusive sense, as opposed to an exclusive or exhaustive sense; that is to say, in the sense of "including, but not limited to."

As used herein, the terms "connected," "coupled," or any variant thereof, means any connection or coupling, either direct or indirect, between two or more elements; the coupling of or connection between the elements can be physical, logical, or a combination thereof. For example, two components may be coupled directly to one another or via one or more intermediary channels or components. As another example, devices may be coupled in such a way that information can be passed therebetween, while not sharing any physical connection with one another. Where context permits, words in the Detailed Description using the singular or plural form may also include the plural or singular form, respectively.

The foregoing description of various embodiments of the described subject matter has been provided for the purposes of illustration and description. It is not intended to be exhaustive or to limit the described subject matter to the precise forms disclosed. Many modifications and variations will be apparent to one skilled in the art. Embodiments were chosen and described in order to best describe the principles of the invention and its practical applications, thereby enabling those skilled in the relevant art to understand the described subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by this disclosure. Particular terminology used when describing certain features or aspects of various embodiments should not be taken to imply that the terminology is being redefined herein to be restricted to any specific parameters, features, or aspects of the technology with which that terminology is associated. In general, the terms used in the following described should not be construed to limit the technology to the specific embodiments disclosed in the specification, unless those terms are explicitly defined herein. Accordingly, the actual scope of the technology encompasses not only the disclosed claims but also all equivalent ways of practicing or implementing the embodiments.

The invention claimed is:

1. A computer-implemented method comprising:
   receiving, by a processor, over a communications network, a plurality of indications of activities of a plurality of users of a coaching service,
      wherein the activities relate to a plurality of resources allocated to the plurality of users, the plurality of resources including a plurality of time increments that provide access to a virtual coach of a coaching service and a plurality of physiological monitoring devices,
      wherein the plurality of indications includes physiological parameter data generated by the plurality of physiological monitoring devices, and
      wherein the plurality of resources is allocated to the plurality of users in accordance with respective coaching protocols associated with the virtual coach of the coaching service;
   processing, by the processor, the plurality of indications of the activities with a dynamic resource allocation engine to:
      compare the plurality of indications of the activities to a threshold utilization value, and
      determine, based on the comparison, a likelihood that a reallocation of a resource can increase utilization of the coaching service without inhibiting the coaching protocols of the plurality of users,
         wherein the dynamic resource allocation engine includes a machine learning algorithm that is trained based on an aggregate of indications of user activities and is configured to model when and what resource to allocate; and
   based on an output of the dynamic resource allocation engine including the determined likelihood, effecting, by the processor, dynamic reallocation of assignments of the plurality of resources to scale the coaching service.

2. The method of claim 1 further comprising, prior to receiving the plurality of indications of the activities:
   allocating the plurality of resources to the plurality of users including a first user and a second user,
      wherein the plurality of resources includes the plurality of time increments that authorize access to the virtual coach and the plurality of physiological monitoring devices, each configured to monitor a physiological parameter when worn by a respective user.

3. The method of claim 2, wherein a first resource includes a first time increment of the virtual coach that is allocated to the first user and a second resource includes a second time increment of the virtual coach that is allocated to the second user, the virtual coach being accessible by the plurality of users for a limited time period.

4. The method of claim 3, wherein a first activity indicates utilization of the coaching service during the first time increment by the first user and a second activity indicates utilization of the coaching service during the second time increment by the second user.

5. The method of claim 4, wherein the dynamic reallocation comprises:
   reallocating at least a portion of the first time increment from the first user to the second user when the utilization of the first time increment is less than the utilization of the second time increment.

6. The method of claim 4, wherein the first activity and the second activity include user inputs responsive to a reoccurring polling process of the plurality of users by the coaching service.

7. The method of claim 3 further comprising, prior to effecting the dynamic reallocation:
   identifying a target user of the plurality of users;
   deallocating assignment of the first resource from the first user or the second resource from the second user; and
   allocating assignment of the deallocated first resource or the deallocated second resource to the target user.

8. The method of claim 3, wherein assignment of the first resource is dynamically reallocated to a target user of the plurality of users based on a physiological parameter of the target user monitored by a physiological monitoring device worn by the target user.

9. The method of claim 2, wherein effecting the dynamic reallocation comprises:
ranking the plurality of resources based on a measure of availability or criticality;
prioritizing the plurality of users based on a measure of effective utilization of the plurality of resources; and
recommending a reallocation of the plurality of resources among the plurality of users based on the ranking of the plurality of resources and the prioritization of the plurality of users.

10. The method of claim 2, wherein effecting the dynamic reallocation comprises:
separating the plurality of users into a plurality of groups, each group associated with a characteristic that is common to all users of the group; and
reallocating at least some of the plurality of resources on a per group basis.

11. The method of claim 2, wherein the first user is a diabetic user and a first coaching protocol includes a diabetes management program for the diabetic user.

12. The method of claim 1, wherein effecting the dynamic reallocation comprises:
presenting an indication of a set of resources to the virtual coach, the set of resources being available for reallocation; and
receiving an indication that the virtual coach selected a resource from among the set of resources for a target user of the plurality of users.

13. A computer-implemented method comprising:
allocating, by a processor, a pool of resources of a coaching service to a plurality of users that subscribe to the coaching service, the pool of resources including a virtual coach, a time increment of a virtual coach session, and a medical device;
processing, by the processor, indications of activities, associated with the allocated pool of resources, with a dynamic resource allocation engine to:
compare the plurality of indications of the activities to a threshold utilization value, and
determine, based on the comparison, a likelihood that reallocation of at least one time increment can increase utilization of the coaching service without inhibiting coaching of the plurality of users,
wherein the dynamic resource allocation engine includes a machine learning algorithm that is trained based on an aggregate of indications of activities and is configured to model when and what resource to allocate;
identifying by the processor, based on an output of the dynamic resource allocation engine, a target user of the plurality of users as having a historically higher utilization rate of at least some of the pool of resources compared to other users that have been allocated resources of the pool of resources;
upon identifying the target user, deallocating by the processor, assignment of a target resource from another user of the plurality of users; and
dynamically reallocating, by the processor, assignment of the deallocated target resource to the target user.

14. The method of claim 13, wherein the target user is identified based on an ongoing physiological measurement calculated by a sensor of a monitoring device worn by the target user.

15. The method of claim 13, wherein deallocating the target resource comprises:
throttling a function or intensity of a medical service based on real-time or near real-time monitoring of a physiological parameter.

16. The method of claim 13, wherein the target user is identified based on at least one of standard clinical data, a prescription profile, a risk profile including a risk score based on amount or frequency of related events, or a self-identified measure of confidence to manage a disease.

17. The method of claim 13, wherein the target user is identified based on an activity profile of the user including a level of engagement with the coaching service over a selected time increment.

18. The method of claim 13, wherein the allocation is based on a unique factor of the target user, sensor data associated with the target user, an availability of a resource, or a global factor of the plurality of users.

19. A server computer comprising:
one or more memories storing instructions of a coaching service that is configured to initiate a coaching session over a computer network for a virtual coach of a plurality of coaching recipients,
wherein each coaching recipient is a user of a computer device capable of coupling to the server computer over the computer network;
one or more processors configured to execute the instructions stored on the one or more memories, causing each computing device to:
allocate a plurality of time increments of the coaching service to the plurality of coaching recipients over the computer network;
process, by a dynamic resource allocation engine, indications of activities associated with the allocated plurality of time increments including causing the server computer to:
compare the indications of the activities to a threshold utilization value, and
determine, based on the comparison, a likelihood that reallocation of at least one time increment can increase utilization of the coaching service without inhibiting coaching of a plurality of users,
wherein the dynamic resource allocation engine includes a machine learning algorithm that is trained based on an aggregate of indications of activities and is configured to model when and what resource to allocate;
identify, based on an output of the dynamic resource allocation engine, a target coaching recipient of the plurality of coaching recipients as having a greater value of a metric relative to at least some of the plurality of coaching recipients; and
dynamically reallocate at least some of the plurality of time increments to the target coaching recipient from another coaching recipient with a lower value of the metric.

20. The server computer of claim 19, wherein the target coaching recipient is identified based on an activity profile of the coaching service.

21. The method of claim 1, wherein the machine learning algorithm includes a Naïve Bayes Classifier algorithm, a K Means Clustering algorithm, a Support Vector Machine algorithm, or an artificial neural network.

* * * * *